(12) United States Patent
Helland et al.

(10) Patent No.: US 6,640,136 B1
(45) Date of Patent: Oct. 28, 2003

(54) IMPLANTABLE CARDIAC STIMULATION DEVICE WITH AUTOMATIC ELECTRODE SELECTION FOR AVOIDING CROSS-CHAMBER STIMULATION

(75) Inventors: John R. Helland, Saugus, CA (US); Gene A. Bornzin, Simi Valley, CA (US)

(73) Assignee: Pacesetters, Inc., Sylmar, CA (US)

( * ) Notice: Subject to any disclaimer, the term of this patent is extended or adjusted under 35 U.S.C. 154(b) by 204 days.

(21) Appl. No.: 09/953,458

(22) Filed: Sep. 12, 2001

(51) Int. Cl.⁷ .................. A61N 1/368; A61N 1/362
(52) U.S. Cl. ........................................................ 607/28
(58) Field of Search ................................. 607/9, 28

(56) References Cited

U.S. PATENT DOCUMENTS

| | | | |
|---|---|---|---|
| 4,365,639 A | 12/1982 | Goldreyer | 128/786 |
| 5,265,601 A | 11/1993 | Mehra | 607/9 |
| 5,350,410 A | 9/1994 | Kleks et al. | 607/28 |
| 5,466,254 A | 11/1995 | Helland | 607/123 |
| 5,545,204 A | 8/1996 | Cammilli et al. | 607/123 |
| 5,999,853 A | 12/1999 | Stoop et al. | 607/9 |
| 6,067,471 A | 5/2000 | Warren | 607/5 |
| 6,081,748 A | 6/2000 | Struble et al. | 607/9 |
| 6,122,545 A | 9/2000 | Struble et al. | 607/9 |
| 6,205,357 B1 | 3/2001 | Ideker et al. | 607/14 |
| 6,546,288 B1 * | 4/2003 | Levine | 607/28 |

* cited by examiner

Primary Examiner—Carl H. Layno

(57) ABSTRACT

An implantable cardiac stimulation device in which cross-chamber stimulation is avoided. The present device is intended for use an implantable device that is intended to stimulate one or more cardiac chambers, for example, in a dual-chamber or multi-chamber device. According to one illustrative embodiment of the device, capture thresholds are determined for a first chamber that is intended to be captured, and also for a second chamber that is not intended to be captured. The stimulation energy is then set to a level based upon the respective capture thresholds.

38 Claims, 7 Drawing Sheets

IMPLANTABLE CARDIAC STIMULATION DEVICE WITH AUTOMATIC ELECTRODE SELECTION FOR AVOIDING CROSS-CHAMBER STIMULATION

FIELD OF THE INVENTION

The present invention relates to dual chamber or multi-chamber implantable cardiac stimulation devices. More specifically, the present invention relates to an implantable cardiac stimulation device with which a coronary sinus lead is used to stimulate the left heart chambers and in which a method is incorporated for automatically selecting left atrial and left ventricle stimulation electrode configurations such that the risk of cross-chamber stimulation is minimized.

BACKGROUND OF THE INVENTION

The technology of cardiac pacemakers has become highly sophisticated with increased features, programmability, and automatization. The current generation of cardiac pacemakers incorporates microprocessors and related circuitry to sense and stimulate heart activity under a variety of physiological conditions. These pacemakers may be programmed to control the heart in correcting or compensating for various heart abnormalities that may be encountered in individual patients. It is a primary goal of programmable, multiple-mode, demand-type cardiac pacemakers to accommodate the changing requirements of a diseased or malfunctioning heart.

For example, proper synchronization of the atrial and ventricular contractions can be important in achieving normal cardiac output. In some patients, this synchrony is disrupted when the normal conduction pathway between the atria and ventricles becomes blocked due to disease. Dual chamber pacemakers are commonly used to treat such complete or intermittent heart block by maintaining atrio-ventricular (AV) synchrony. Atrial activity is monitored for evidence of a P-wave, which is the electrical depolarization occurring in the atrial myocardium producing atrial contraction. Ventricular activity is monitored for evidence of an R-wave, which is the electrical depolarization occurring in the ventricular myocardium producing ventricular contraction. In a normal heart, the electrical impulse producing the intrinsic P-wave is conducted to the ventricles with an inherent delay such that the resulting R-wave causes the ventricles to contract just after the atria have contracted. Effective cardiac output is thus achieved by allowing the atria to contract first, filling the ventricles with blood, followed by the more powerful contraction of the ventricles, which eject blood throughout the body. If the normal conduction pathways responsible for triggering and synchronizing these contractions are blocked, a dual-chamber pacemaker, upon sensing the absence of a P-wave or R-wave or both, will deliver a stimulation pulse to the atrium or ventricle or both. The ventricular pulse is delivered after a given time interval, called the "AV delay," following the atrial P-wave (or atrial stimulation pulse) in order to maintain proper atrial-ventricular synchrony.

The stimulating pulse must be of sufficient energy to cause depolarization of the cardiac tissue and the subsequent contraction of the stimulated heart chamber. This condition is known as "capture." The lowest stimulation energy required to achieve capture is referred to as the capture "threshold."

Most dual-chamber (or DDD) stimulation systems utilize two leads, one connected to the atrial chamber and one connected to the ventricular chamber, to provide electrical contact for stimulating and sensing in both chambers. Each lead is connected to the appropriate channel, atrial or ventricle, of the cardiac stimulation system.

Programmability has been incorporated into cardiac stimulation devices to select the polarity of the electrodes to be used in sensing and stimulation. A unipolar lead is one in which stimulation occurs between the cathode tip and the device housing, also referred to as a "case electrode", that serves as the anode. A bipolar lead is one in which stimulation occurs between the cathode tip, and an anode ring electrode spaced approximately one to two centimeters from the cathode tip.

Unipolar or bipolar leads implanted in conjunction with conventional stimulation systems can be anchored in such a way that the tip electrodes can be positioned in contact with the targeted cardiac tissue. Intravenous leads can be advanced into the right chambers of the heart to position electrodes for stimulation and sensing in the right ventricle. The lead can be anchored in the thick muscular wall near the ventricular apex. Since the anatomical structure of the atria makes it more difficult to anchor a lead in the atrial wall, active fixation, such as a "screw-in" type lead, is often used. In some cases, "floating" multi-electrode lead bodies have been designed in a way that a single unipolar electrode or a bipolar pair of electrodes on the lead body remain within the blood volume of the right atrial chamber for sensing and stimulation in the atrium. Electrodes near the distal tip of the lead make contact with the ventricular tissue. Reference is made to U.S. Pat. No. 5,999,853 to Stoop et al.

There are numerous advantages for using a single, multi-electrode lead rather than two separate leads. Lower cost, shorter implantation time, and reduced complexity and cost of a stimulation system requiring only one lead connection are all benefits associated with a single lead.

For delivering stimulation therapies in the left heart, coronary sinus leads have been developed that may be advanced through the right atrium, the coronary sinus and into the coronary veins to access the left atrium (LA) and left ventricle (LV). Refer to U.S. Pat. No. 5,466,254 to Helland which is incorporated herein by reference. By advancing a multi-electrode coronary sinus lead, dual chamber stimulation and sensing as well as cardioversion therapy may be delivered in the left heart chambers with placement of only a single lead. While this has many advantages, it is known that coronary sinus leads can be difficult to place. Care must be taken to advance the lead such that the final electrode positions result in acceptable capture thresholds. Coronary sinus leads can shift from their original locations after implantation with each shift potentially causing small but clinically significant changes in capture thresholds or in sensing of cardiac signals. An increase in capture threshold may result in loss of capture, an undesirable situation.

Another problem encountered in using coronary sinus leads is "cross-chamber stimulation." Cross-chamber stimulation occurs when the stimulation pulse energy applied to capture one chamber of the heart, for example the left ventricle, is high enough to capture a second chamber of the heart, for example the left atrium. Simultaneous capture of the atrium and the ventricle is highly undesirable in that it will cause the chambers to contract against each other leading to severe cardiac output perturbation. The common practice of applying a working margin to the programmed stimulation energy to allow for fluctuation in capture threshold can inadvertently cause the stimulating energy to be high enough for cross-chamber capture.

In U.S. Pat. No. 5,265,601 to Mehra, a method for dual chamber cardiac stimulation and sensing using a single lead is proposed. The atrium is paced using a stimulation energy that is below the capture threshold for the ventricle but still high enough to capture the atrium. Since atrial and ventricular capture thresholds can be similar, the ventricular stimulation pulse is delivered following a short atrial-ventricular (AV) delay in order to avoid atrial capture. In this way, the ventricular pulse is delivered during the physiological absolute refractory period of the atria making inadvertent atrial cross-capture impossible. The limitation to this approach is a limited atrial-ventricular (AV) delay. The AV delay must be kept short enough to ensure ventricular stimulation occurs within the atrial refractory period. Such a short AV interval may not be the most hemodynamically effective and may not allow time for naturally occurring R-waves to be conducted. Inadvertent cross-capture of the ventricle during atrial stimulation is not necessarily avoided by this approach.

Ideally, stimulation of the left atrium and the left ventricle using a multi-polar lead positioned in the coronary sinus region would allow electrode polarities to be selected such that an electrode pair giving the lowest left atrial threshold and highest left ventricular threshold is selected for left atrial stimulation. Likewise, an electrode pair giving the lowest left ventricular threshold and highest left atrial threshold is selected for left ventricular stimulation. In this way, the risk of cross-chamber stimulation is minimized, and battery current drain is minimized. However, testing for these optimal electrode combinations can be time-consuming, and these optimal combinations may constantly change over time with either shifts of the coronary sinus lead location or other physiological factors.

It would thus be desirable to provide an implantable dual chamber or multi-chamber cardiac stimulation system possessing means for automatically measuring capture thresholds in each cardiac chamber using all available electrode combinations from one or more multi-polar leads. Further, it would be desirable to determine the likelihood of cross-chamber capture by measuring the threshold for cross-chamber capture from the electrode pairs available. It would also be desirable to provide a stimulation system that, based on these threshold measurements, automatically selects the optimal electrode configuration for stimulating in each chamber.

SUMMARY OF THE INVENTION

The present invention addresses these problems and more by providing an implantable cardiac stimulation device in which cross-chamber stimulation is avoided. The present invention is intended for use an implantable device that is intended to stimulate one or more cardiac chambers, for example, in a dual-chamber or multi-chamber device. According to one illustrative embodiment of the invention, capture thresholds are determined for a first chamber that is intended to be captured, and also for a second chamber that is not intended to be captured. The stimulation energy is then set to a level to capture the first chamber and to not capture the second chamber.

In one embodiment, the present invention includes a cardiac stimulation system capable of automatically determining which electrodes on a multi-polar coronary sinus lead can be used to safely stimulate the left atrium and/or the left ventricle separately without stimulating both the left atrium and the left ventricle at the same time.

The foregoing and other features of the present invention are realized by providing an implantable cardiac stimulation device equipped with cardiac data acquisition capabilities. A preferred embodiment of the stimulation device includes a control system for controlling the operation of the device and executing various test algorithms including capture threshold tests and cross-capture threshold tests; a set of leads including at least a multi-polar coronary sinus lead for receiving cardiac signals from the left atrium and left ventricle and delivering stimulation pulses in the left atrium and left ventricle; a set of sensing circuits comprised of sense amplifiers for sensing and amplifying the cardiac signals; and a set of pulse generators for generating atrial and ventricular stimulation pulses. In addition, the device includes memory for storing operational parameters for the control system and storing data such as a capture threshold test results. The device also includes a telemetry circuit for communicating with an external programmer.

In a preferred embodiment, cross-chamber stimulation is avoided by the present invention by performing the following three operations automatically: 1) determining the left atrial and left ventricular capture thresholds using all electrode combinations available on one or more multi-polar leads positioned in the region of the coronary sinus; 2) using these same electrode combinations, determine the cross-chamber capture thresholds beginning with the electrode combinations resulting in the lowest left atrial and left ventricular capture thresholds; and 3) selecting the optimal electrode configurations for left atrial and left ventricular stimulation based on these testing results. Preferably the electrode configuration selected for left atrial stimulation is one resulting in the lowest atrial capture threshold and a cross-capture threshold greater than the atrial capture threshold plus a working margin. Likewise, the electrode configuration selected for left ventricular stimulation is one resulting in the lowest ventricular capture threshold and a cross-capture threshold greater than the ventricular capture threshold plus a working margin.

Thus, safe effective stimulation of each left heart chamber is provided in a way that ensures proper atrial-ventricular synchrony with a minimal risk of cross-chamber capture and uses the minimum battery energy required.

BRIEF DESCRIPTION OF THE DRAWINGS

Further features and advantages of the present invention may be more readily understood by reference to the following description taken in conjunction with the accompanying drawings, in which.

DESCRIPTION OF THE PREFERRED EMBODIMENTS

The following description is of a best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

As indicated above, the present invention relates primarily to a cardiac stimulation device capable of avoiding cross-chamber stimulation by automatically determining a suitable stimulation energy to capture a first chamber while not capturing any other chamber. According to one illustrative embodiment of the invention, capture thresholds are determined for the first chamber and for a second chamber, and the stimulation energy is then set to an appropriate level to capture the first chamber and not capture the second chamber.

The first chamber can be any of the heart chambers, including either atrium or either ventricle. Likewise, the second chamber can be any of the four heart chambers. For example, the first chamber can be the right or left atrium, while the second chamber is the right or left ventricle. Conversely, the first chamber can be the right or left ventricle, while the second chamber is the right or left atrium.

In one embodiment, the present invention is preferably implemented in an implantable dual-chamber or multi-chamber cardiac stimulation device employing a multi-polar coronary sinus lead for stimulating the left heart chambers. The methods of the present invention may be implemented in any implantable cardiac stimulation device that is at least capable of sensing and stimulating the left chambers of the heart. A detailed description is provided, in conjunction with FIGS. 1 and 2, of one embodiment of an implantable cardiac stimulation device with associated leads in which the methods of the present invention may be implemented.

Figure 1:
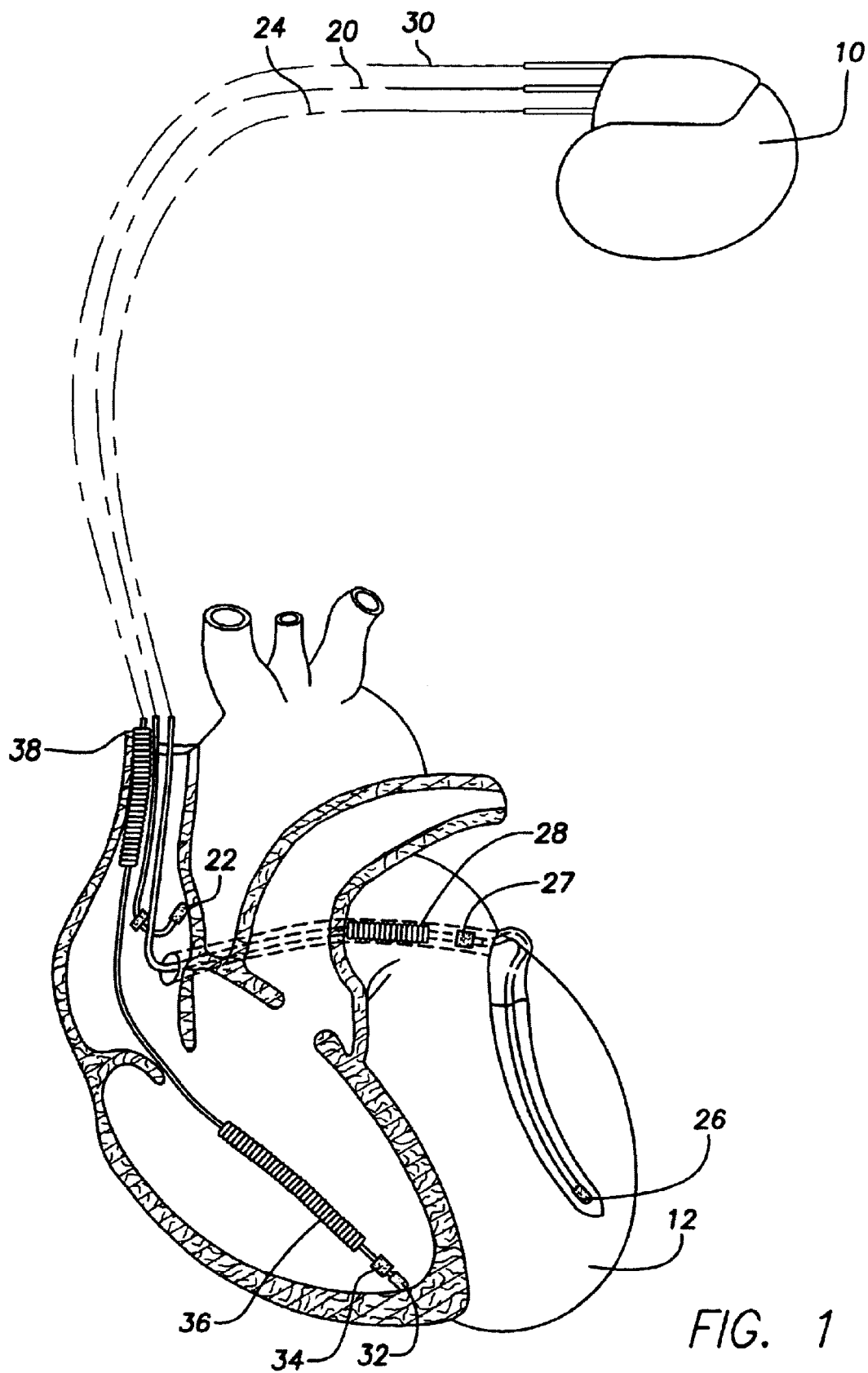
FIG. 1 is a simplified, partly cutaway view illustrating an implantable stimulation device in electrical communication with at least three leads implanted into a patient's heart for delivering multi-chamber stimulation and shock therapy.

FIG. 1 illustrates a stimulation device 10 in electrical communication with a patient's heart 12 by way of three leads 20, 24 and 30 suitable for delivering multi-chamber stimulation and shock therapy. To sense right atrial cardiac signals and to provide right atrial chamber stimulation therapy, the stimulation device 10 is coupled to an implantable right atrial lead 20 having at least an atrial tip electrode 22, which typically is implanted in the patient's right atrial appendage. The right atrial lead 20 may also have an atrial ring electrode 23 to allow bipolar stimulation or sensing in combination with the atrial tip electrode 22.

To sense left atrial and ventricular cardiac signals and to provide left-chamber stimulation therapy, the stimulation device 10 is coupled to a "coronary sinus" lead 24 designed for placement in the "coronary sinus region" via the coronary sinus ostium so as to place a distal electrode adjacent to the left ventricle and additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the coronary sinus lead 24 is designed to receive atrial and ventricular cardiac signals and to deliver: left ventricular stimulation therapy using at least a coronary sinus tip electrode 26, left atrial stimulation therapy using at least a coronary sinus ring electrode 27, and shocking therapy using at least a coronary sinus coil electrode 28. For a complete description of a coronary sinus lead, refer to U.S. patent application Ser. No. 09/457,277, titled "A Self-Anchoring, Steerable Coronary Sinus Lead" (Pianca et. al), and U.S. Pat. No. 5,466,254, titled "Coronary Sinus Lead with Atrial Sensing Capability"(Helland), and U.S. Pat. No. 5,545,204 titled "Sequential cardiostimulation system" (DDD) using a single electrocatheter inserted through the coronary sinus (Cammilli, et al.), which are hereby incorporated herein by reference.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the right atrium and/or superior vena cava. Accordingly, the right ventricular lead 30 is capable of receiving cardiac signals, and delivering stimulation in the form of pacing and shock therapy to at least between the right ventricle and the right atrium, between a housing 40 and the right ventricle for defibrillation shock therapies, or between the right ventricular shock electrode 36 and the combination of the housing 40 and the right atrial shock electrode 38.

Figure 2:
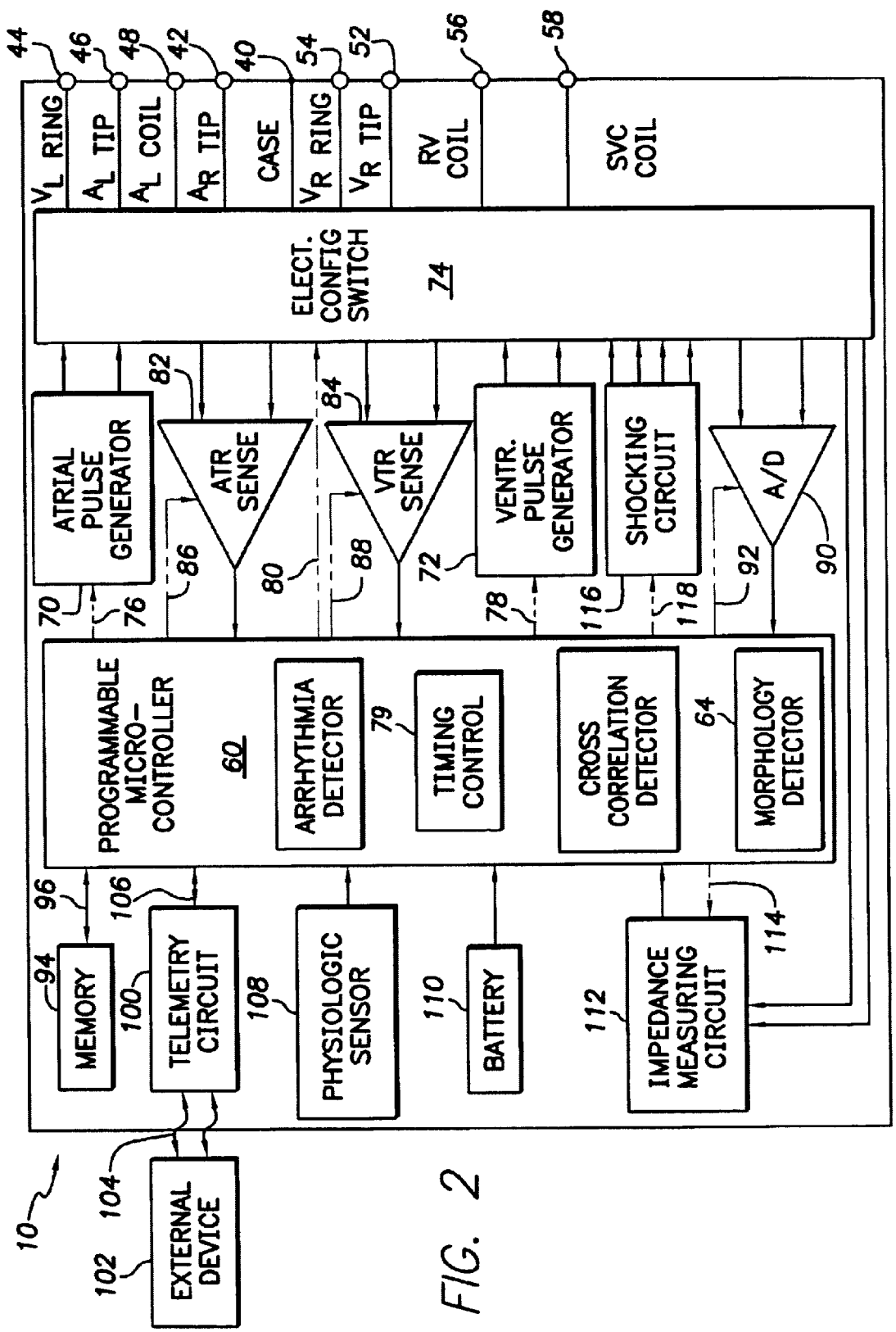
FIG. 2 is a functional block diagram of the multi-chamber implantable stimulation device of FIG. 1, illustrating the basic elements that provide cardioversion, defibrillation and pacing stimulation in four chambers of the heart.

FIG. 2 illustrates a simplified block diagram of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The stimulation device 10 includes a housing 40 which is often referred to as "can", "case" or "case electrode", and which may be programmably selected to act as the return electrode for all "unipolar" stimulation modes. The housing 40 may further be used as a return electrode alone or in combination with one or more of the coil electrodes 28, 36, or 38, for defibrillation shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and stimulation, the connector includes at least a right atrial tip terminal 42 adapted for connection to the atrial ($A_R$) tip electrode 22. The connector may also include a right atrial ring terminal ($A_R$ RING) 43 for connection to the atrial ring electrode 23.

To achieve left chamber sensing, pacing and shocking, the connector includes at least a left ventricular ($V_L$) tip terminal 44, a left atrial ($A_L$) ring terminal 46, and a left atrial ($A_L$) shocking terminal (coil) 48, which are adapted for connection to the coronary sinus tip electrode 26, the coronary sinus tip electrode 27, and the coronary sinus coil electrode 28, respectively.

To support right chamber sensing, pacing and shocking, the connector further includes a right ventricular ($V_R$) tip terminal 52, a right ventricular ($V_R$) ring terminal 54, a right ventricular (RV) shocking terminal (coil) 56, and an SVC shocking terminal (coil) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 that controls the various modes of stimulation therapy. As is well known in the art, the microcontroller 60 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate stimulation pulses for delivery by the right atrial lead 20, the right ventricular lead 30, and/or the coronary sinus lead 24 via a switch 74. It is understood that in order to provide stimulation therapy in each of the four chambers of the heart, the atrial pulse generator 70 and the ventricular pulse generator 72 may include dedicated, independent pulse generators, multiplexed pulse generators, or shared pulse generators. The atrial pulse generator 70 and the ventricular pulse generator 72 are controlled by the microcontroller 60 via appropriate control signals 76 and 78, respectively, to trigger or inhibit the stimulation pulses.

The microcontroller 60 further includes timing control circuitry 79 which is used to control the timing of such stimulation pulses (e.g. pacing rate, atrio-ventricular (AV) delay, atrial interconduction (A-A) delay, or ventricular interconduction (V-V) delay, etc.), as well as to keep track of the timing of refractory periods, PVARP intervals, noise detection windows, evoked response windows, alert intervals, marker channel timing, etc.

The switch bank 74 includes a plurality of switches for connecting the desired electrodes to the appropriate I/O circuits, thereby providing complete electrode programmability. Accordingly, the switch bank 74, in response to a control signal 80 from the microcontroller 60, determines the polarity of the stimulation pulses (e.g. unipolar, bipolar, combipolar, etc.) by selectively closing the appropriate combination of switches (not shown).

Atrial sensing circuits 82 and ventricular sensing circuits 84 may also be selectively coupled to the right atrial lead 20, coronary sinus lead 24, and the right ventricular lead 30, through the switch bank 74, for detecting the presence of cardiac activity in each of the four chambers of the heart. Accordingly, the atrial and ventricular sensing circuits 82 and 84 may include dedicated sense amplifiers, multiplexed amplifiers, or shared amplifiers. The switch bank 74 determines the "sensing polarity" of the cardiac signal by selectively closing the appropriate switches. In this way, the clinician may program the sensing polarity independent of the stimulation polarity.

Each of the atrial sensing circuit 82 or the ventricular sensing circuit 84 preferably employs one or more low power, precision amplifiers with programmable gain and/or automatic gain control, bandpass filtering, and a threshold detection circuit, to selectively sense the cardiac signal of interest. The automatic gain control enables the stimulation device 10 to deal effectively with the difficult problem of sensing the low amplitude signal characteristics of atrial or ventricular fibrillation.

The outputs of the atrial and ventricular sensing circuits 82 and 84 are connected to the microcontroller 60 for triggering or inhibiting the atrial and ventricular pulse generators 70 and 72, respectively, in a demand fashion, in response to the absence or presence of cardiac activity, respectively, in the appropriate chambers of the heart.

For arrhythmia detection, the stimulation device 10 utilizes the atrial and ventricular sensing circuits 82 and 84 to sense cardiac signals, for determining whether a rhythm is physiologic or pathologic. As used herein "sensing" is reserved for the noting of an electrical signal, and "detection" is the processing of these sensed signals and noting the presence of an arrhythmia. The timing intervals between sensed events (e.g. P-waves, R-waves, and depolarization signals associated with fibrillation which are sometimes referred to as "F-waves" or "Fib-waves") are then classified by the microcontroller 60 by comparing them to a predefined rate zone limit (e.g. bradycardia, normal, low rate VT, high rate VT, and fibrillation rate zones) and various other characteristics (e.g. sudden onset, stability, physiologic sensors, and morphology, etc.) in order to determine the type of remedial therapy that is needed (e.g. bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into digital signals, and store the digital signals for later processing and/or telemetric transmission to an external device 102. The data acquisition system 90 is coupled to the right atrial lead 20, the coronary sinus lead 24, and the right ventricular lead 30 through the switch bank 74 to sample cardiac signals across any pair of desired electrodes.

Advantageously, the data acquisition system 90 may be coupled to the microcontroller 60 or another detection circuitry, for detecting an evoked response from the heart 12 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 60 detects a depolarization signal during a window following a stimulation pulse, the presence of which indicates that capture has occurred. The microcontroller 60 enables capture detection in the ventricles by triggering the ventricular pulse generator 72 to generate a stimulation pulse, starting a capture detection window using the timing circuitry within the microcontroller 60, and enabling the data acquisition system 90 via control signal 92 to sample the cardiac signal that falls in the capture detection window as sensed by ventricular sense circuitry 84 and, based on the amplitude and/or frequency of the sampled cardiac signal, determines if capture has occurred. Atrial capture detection is performed similarly.

Capture detection may occur on a beat-by-beat basis or on a sampled basis during normal pacing operation of device 10. In addition, a capture threshold search may be performed whenever capture detection determines that capture has been lost. A capture threshold search may also be performed on a programmed periodic basis. In one embodiment, a threshold search is performed once a day during at least the acute phase (e.g. the first 30 days) and less frequently thereafter. A capture threshold search would begin at a desired starting point (either a high energy level or the level at which capture is currently occurring) and then the energy level would be decreased until capture is lost. The value at which capture is lost is known as the capture threshold. Thereafter, a working margin is added to the capture threshold to set the final stimulation energy level in order to provide stimulation safely above the threshold level. For a more detailed description of the implementation of capture detection circuitry and algorithms refer, for example, to U.S. Pat. No. 5,350,410 (Mann et. al), which is incorporated herein by reference.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, stimulation pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy. A feature of the present invention is the ability to sense and store a relatively large amount of data (e.g. from the data acquisition system 90), which data may then be used for subsequent analysis to guide the programming of the stimulation device 10.

Advantageously, the operating parameters of the stimulation device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller 60 by a control signal 106. The telemetry circuit 100 advantageously allows intracardiac electrograms and status information relating to the operation of the stimulation device 10 (as contained in the microcontroller 60 or memory 94) to be sent to the external device 102 through the established communication link 104.

In a preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g. detecting sleep and wake states). Accordingly, the microcontroller 60 responds by adjusting the various pacing parameters (such as rate, AV Delay, V-V Delay, etc.) at which the atrial and ventricular pulse generators 70 and 72 generate stimulation pulses. Physiologic sensor 108 is not critical to the present invention and is shown only for sake of completeness.

The stimulation device 10 additionally includes a power source such as a battery 110 that provides operating power to all the circuits shown in FIG. 2. For the stimulation device 10, which employs shocking therapy, the battery 110 must be capable of operating at low current drains for long periods of time and also be capable of providing high-current pulses (for capacitor charging) when the patient requires a shock pulse. The battery 110 must preferably have a predictable discharge characteristic so that elective replacement time can be detected. Accordingly, the stimulation device 10 can employ, for example, lithium/silver vanadium oxide batteries.

As further shown in FIG. 2, the stimulation device 10 is shown as having an impedance measuring circuit 112 which is enabled by the microcontroller 60 by a control signal 114.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high (11 to 40 Joules) energy, as controlled by the microcontroller 60. Such shocking pulses are applied to the patient's heart through at least two shocking electrodes, and as shown in this embodiment, selected from the coronary sinus coil electrode 28, the RV coil electrode 36, and/or the SVC coil electrode 38 (FIG. 1). As noted above, the housing 40 may act as an active electrode in combination with the RV electrode 36, or as part of a split electrical vector using the SVC coil electrode 38 or the coronary sinus coil electrode 28 (i.e., using the RV electrode 36 as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
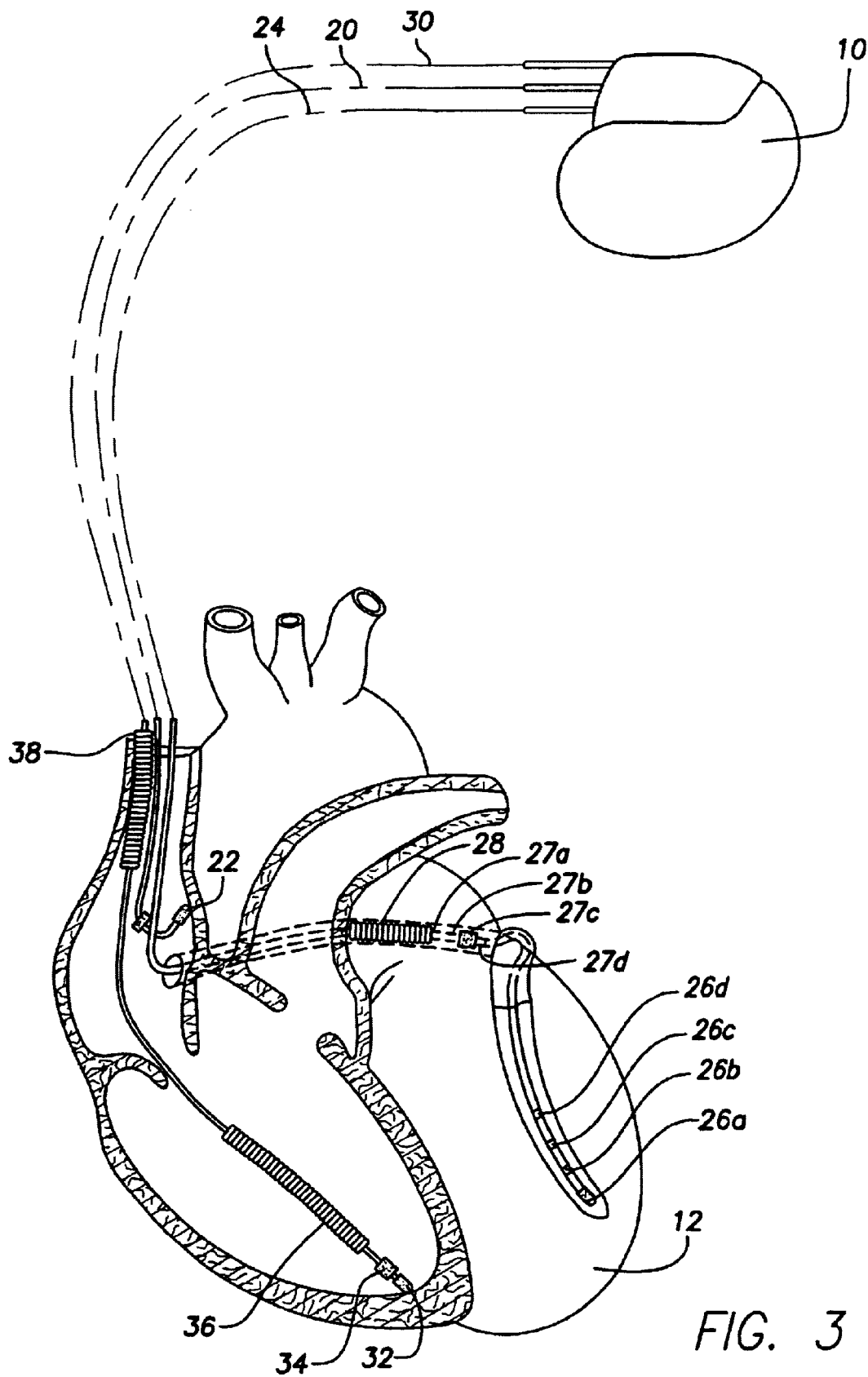
FIG. 3 is a simplified, partly cutaway view illustrating an implantable stimulation device in electrical communication with at least three leads, one of which is a multi-polar coronary sinus lead, implanted into a patient's heart for delivering multi-chamber stimulation and shock therapy according to an alternative embodiment of the present invention.

In accordance with one embodiment of the present invention, coronary sinus lead 24 preferably includes multiple electrodes, each of which may be selectively connected or disconnected by switch 74 thus providing a plurality of unipolar or bipolar combinations for stimulating the left atrium and/or the left ventricle. FIG. 3 illustrates an implanted cardiac stimulation device 10 in communication with the heart with three leads, right atrial lead 20, right ventricular lead 30 and coronary sinus lead 24. In contrast to the system shown in FIG. 1, the coronary sinus lead 24 shown in FIG. 3 possesses a plurality of electrodes for stimulating the left atrium and the left ventricle. In this example, four electrodes 27a, 27b, 27c, and 27d are shown positioned in a location approximately adjacent to the left atrium. An additional four electrodes 26a, 26b, 26c, and 26d are shown positioned approximately adjacent to the left ventricle. Any of these electrodes may be used in combination with housing 40 to perform unipolar stimulation or sensing in the left atrium or left ventricle. Furthermore, any of these electrodes may be used in combination with each other or in combination with the coronary sinus coil electrode 28 to provide sensing or stimulation in either the left atrium or the left ventricle.

In one embodiment, the device utilizes right atrial lead 20 and/or right ventricular lead 30 to determine capture thresholds for the right atrium and right ventricle, and to use such information to set a stimulation energy level in order to capture one chamber (e.g., the right atrium) and not capture the other chamber (e.g., the right ventricle). For example, the stimulating electrode could be placed adjacent to the AV node in the right atrium, and then tested to determine both the atrial capture threshold as well as the ventricular capture threshold, from which a suitable stimulation energy level is selected. This embodiment is disclosed in more detail below.

Figure 4:
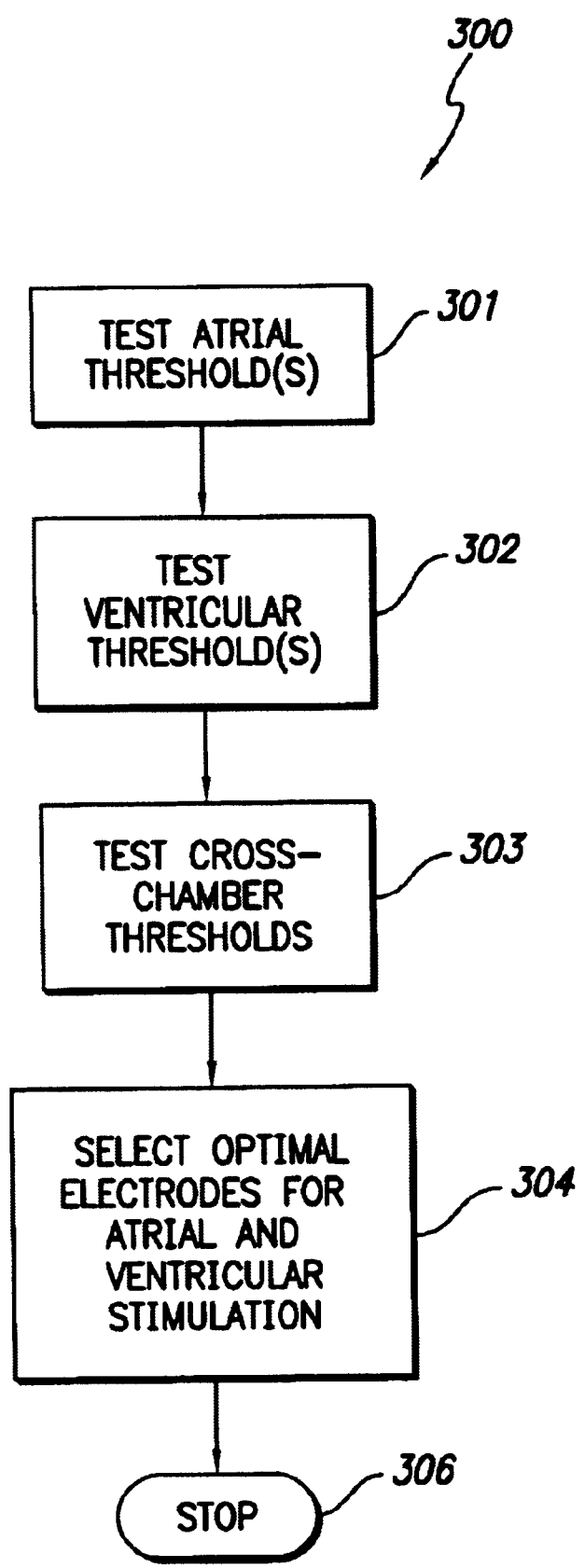
FIG. 4 is a high-level block diagram providing an overview of the operation of one embodiment of the present invention for automatically adjusting the stimulation energy to achieve optimal stimulation in the left atrium and the left ventricle.

In FIG. 4, a flow chart is shown describing an overview of the operation and features implemented in one embodiment of the stimulation device 10 for determining the optimal electrode configurations for left heart stimulation. In this flow chart, and the other flow charts described herein, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

The flow chart of FIG. 4 illustrates a method 300 for determining capture thresholds in the left heart chambers and, based on the threshold results, selecting optimal stimulation electrode configurations. The method 300 may be initiated by a microprocessor 60 upon: 1) receipt of an external command given by a medical practitioner via external device 102, or 2) an internal triggering event, which may be a regular periodic clock interval (e.g. 24 hours) or a loss of capture detection.

Figure 5:
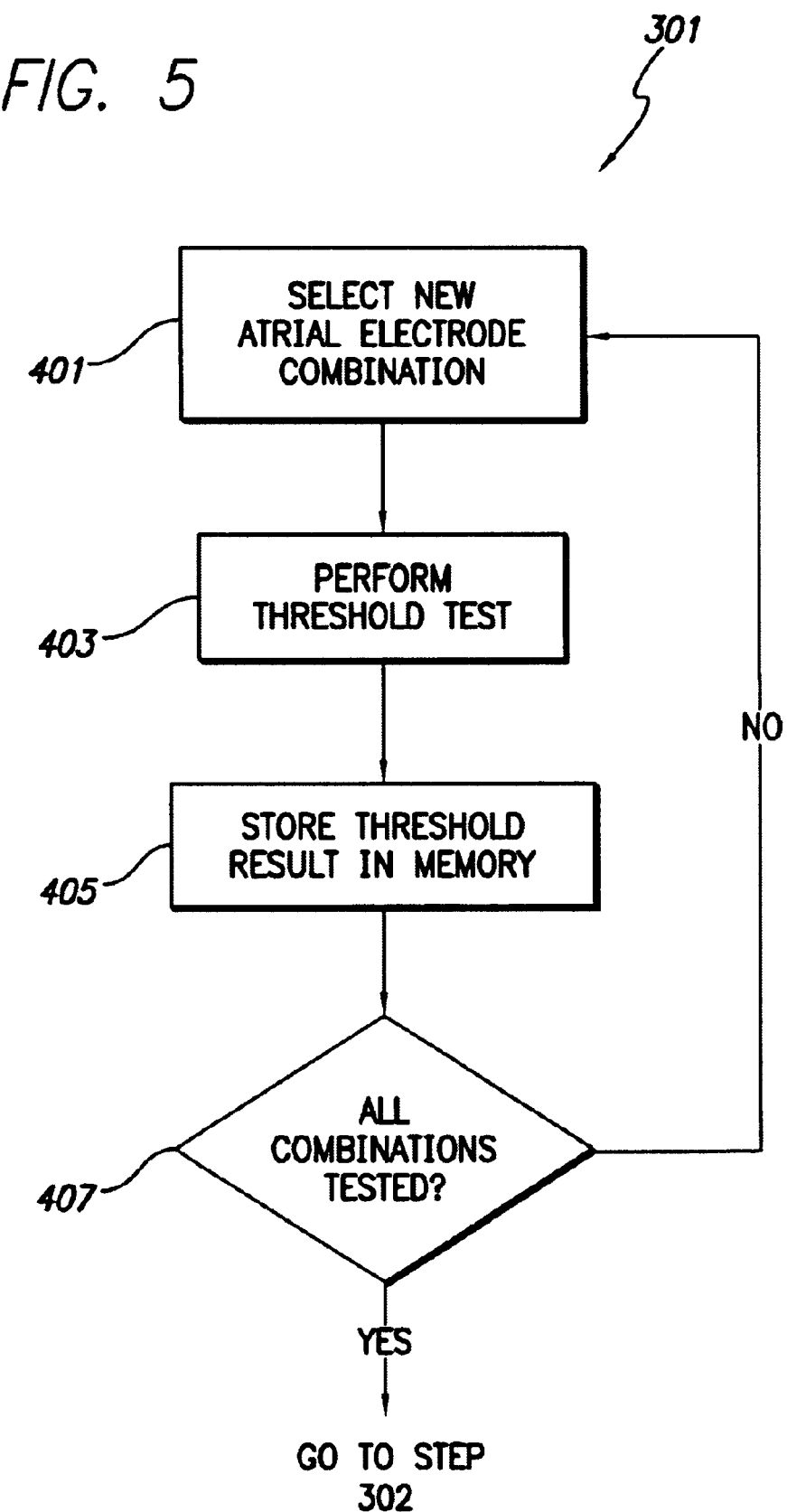
FIG. 5 is a flow chart describing one algorithm that may be used by the present invention during the operations of FIG. 3 for automatically determining left atrial capture threshold.

At step 301, left atrial capture threshold is tested in a manner to be described in greater detail in conjunction with FIG. 5. At step 302, left ventricular capture threshold is tested in a manner to be described in greater detail in conjunction with FIG. 6. At step 303, the threshold required to achieve cross-chamber capture, that is capture of the left atrium and left ventricular simultaneously when delivering a stimulating pulse to only one set of electrodes, is determined in a manner to be described in greater detail in conjunction with FIG. 7.

Finally at step 304, the method 300 automatically selects the optimal electrode configuration for left atrial stimulation and the optimal electrode configuration for left ventricular stimulation in a way that minimizes the risk of cross-chamber capture. Based on the results of steps 301 through 303, the electrode configuration that resulted in the lowest left atrial capture threshold and the highest left ventricular capture threshold is selected as the left atrial stimulation electrode configuration. For example, the method may select the electrode configuration that provides the largest ratio between lowest capture in the desired chamber and highest capture in the non-desired chamber. Alternatively, the method may select the electrode configuration that has the lowest capture threshold in the desired chamber, while also providing a sufficient differential between the two capture thresholds (e.g., some predetermined number of joules between the two capture thresholds). Likewise, the electrode configuration that resulted in the lowest left ventricular capture threshold and the highest left atrial capture threshold is selected as the left ventricular stimulation electrode configuration. Method 300 is subsequently terminated at step 306. The new electrode configurations will remain unchanged until the next time method 300 is enabled either by a periodic trigger generated by microprocessor 60 or by an external command given by a medical practitioner.

In another embodiment of the present invention, device 10 uses a single electrode configuration to determine capture thresholds for both the desired and non-desired chambers, and then sets the stimulation energy to a level such that the desired chamber is captured, while the non-desired chamber is not captured.

Step 301 of the method 300 is illustrated in FIG. 5. Step 301 can be considered a subroutine of method 300 in which device 10 must essentially perform a threshold test using each electrode configuration available for stimulating in the left atrium via coronary sinus lead 24. Thus, at step 401, a new electrode combination is selected. The order in which the electrode combinations are tested is not critical to the operation of the invention. In the embodiment shown in FIG. 1, the unipolar electrode configuration for stimulating the left atrium using coronary sinus ring electrode 27 and the housing 40; the unipolar electrode configuration using coronary sinus coil electrode 28 and housing 40; and the electrode configuration using left atrial ring electrode 27 and coronary sinus coil electrode 28 will be selectively connected, one at a time, by opening and closing the appropriate switches in switch 74.

In the alternative embodiment illustrated in FIG. 3, each coronary sinus ring electrode 27a, 27b, 27c, or 27d may be selected one at a time in a unipolar stimulation configuration with the housing 40 as the return electrode or with coronary sinus coil electrode 28 as the return electrode. In addition, each bipolar combination, available by connecting left atrial ring electrodes 27a, 27b, 27c, or 27d two at a time, may be selected one by one by opening and closing the appropriate switches in switch 74.

It is recognized that numerous electrode combinations may exist, depending on the type of lead(s) and device implanted, which may be used within the scope of the present invention.

As shown in FIG. 5, after selecting one stimulation electrode configuration, a threshold test is performed at step 403. The threshold test may be performed by techniques generally known in the art. A threshold test is performed by setting the stimulation energy to a high or maximum value, expected to be supra-threshold. The stimulation energy is then progressively decreased by decrementing either the pulse width or the pulse amplitude until loss of capture is detected.

Capture verification during the threshold test is generally performed by setting a capture detection window following the stimulation pulse and searching for an evoked response within that window. The evoked response may be detected by a signal that exceeds a predefined sensing threshold, by comparing the sampled signal to a template model of an evoked response, or by other means known in the art.

One feature of the present invention is the ability to set a capture verification window in both the atrial and ventricular channels of device 10 simultaneously. After delivery of a stimulation pulse to the atrium during the threshold test of step 403, a capture detection window is set to detect an evoked response in both the atrium and the ventricle. In this way, cross-chamber capture can be detected.

Sensing during capture verification in the atrium may be performed using the same electrodes as used for stimulation or, preferably, using a different electrode pair to avoid lead polarization effects that occur at the electrode-tissue interface of the stimulating electrodes.

For example, in the implant configuration shown in FIG. 3, when the proximal pair of electrodes 27a and 27b is selected to be tested, the distal pair of electrodes 27c and 27d may be used for sensing. If electrodes 27a and 27c are selected as the test electrodes for stimulation, the electrodes 27b and 27d may be selected as the sensing pair of electrodes, and so forth. Alternatively, one pair of electrodes, such as the coronary sinus coil electrode 28 and the device housing 40, may be designated as the sensing electrodes during all stimulation electrode configuration testing. Simultaneous sensing for cross-chamber capture in the left ventricle may be performed using any designated electrode pair.

The lowest stimulation energy at which capture still occurs is stored in memory 94, at step 405, as the capture threshold for the electrode configuration currently being tested. The threshold is stored with a designator representing the corresponding electrode configuration.

If all electrode combinations for stimulating in the left atrium have not yet been tested as determined at decision step 407, subroutine 301 returns to step 401 to select the next electrode combination for testing. Once all electrode combinations have been tested, with all threshold results stored in memory 94, subroutine 301 returns to the main method 300 and proceeds to step 302.

Figure 6:
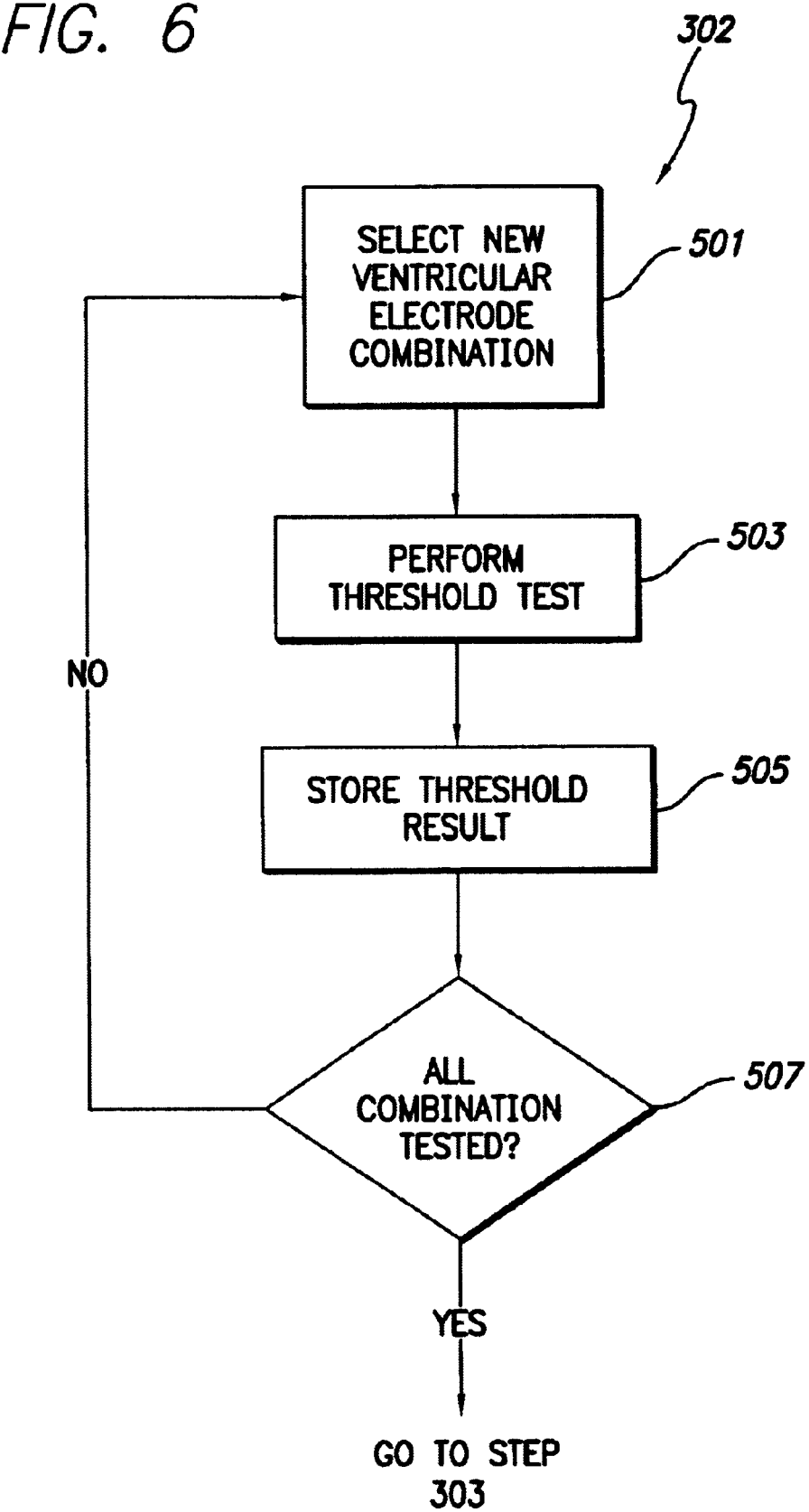
FIG. 6 is a flow chart describing an algorithm that may be used by the present invention during the operations of FIG. 3 for automatically determining left ventricular capture threshold.

Step 302 of method 300 is illustrated in FIG. 6. In step 302, device 10 must essentially perform a threshold test using each electrode configuration available for stimulating in the left ventricle via coronary sinus lead 24. Thus, at step 501, a new left ventricular electrode combination is selected. The order in which the electrode combinations are tested is not critical to the operation of the invention. Referring back to the implant configuration shown in FIG. 1, the unipolar electrode configuration for stimulating the left ventricle using left ventricular tip electrode 26 and the housing 40; the bipolar electrode configuration using left ventricular tip electrode 26 and left atrial ring electrode 27; and the bipolar electrode configuration using left ventricular tip electrode 26 and coronary sinus coil electrode 28 will be selectively connected, one at a time, by opening and closing the appropriate switches in switch 74.

In the alternative embodiment illustrated in FIG. 3, each coronary sinus electrode 26a, 26b, 26c, or 26d may be selected one at a time in a unipolar stimulation configuration with housing 40 as the return electrode or with coronary sinus coil electrode 28 as the return electrode. In addition, each bipolar combination, available by connecting coronary sinus electrodes 26a, 26b, 26c, or 26d two at a time, is selected one-by-one by opening and closing the appropriate switches in switch 74.

As shown in FIG. 6, after selecting one stimulation electrode configuration, a threshold test is performed at step 503 in a manner similar to the method described above for atrial threshold testing. The threshold test may be performed by techniques generally known in the art. Sensing for the evoked response during a capture detection window may be performed between the same electrodes used for stimulation, but is preferably performed between a different electrode pair. Simultaneous sensing in the atrium for detecting cross-chamber capture may be performed using any designated electrode pair.

The lowest stimulation energy at which left ventricular capture still occurred is stored in memory 94, at step 505. Both the capture threshold and a designator indicating the corresponding electrode configuration are stored.

If all electrode combinations for stimulating in the left ventricle have not yet been tested, as determined at decision step 507, subroutine 302 returns to step 501 to select the next electrode combination for testing. Once all electrode combinations have been tested, with threshold results stored in memory 94, subroutine 302 returns to the main method 300 and proceeds to step 303.

The methods of step 301 and 302 for measuring capture thresholds in the left atrium and the left ventricle may be performed in the order indicated or testing may be performed first in the left ventricle and then in the left atrium. The order in which threshold testing is performed is not critical to the successful operation of the invention.

If, at any time during the threshold testing of steps 403 (FIG. 5) or 503 (FIG. 6), capture is detected in the other chamber when loss of capture has occurred in the chamber being tested, then the threshold test is aborted. The electrode configuration being tested is unacceptable for stimulation in the chamber being tested. For example, if threshold testing is being performed in the left atrium and a loss of capture is detected but capture is detected in the left ventricle, the threshold test is aborted. The threshold for capturing the left ventricle in this example is lower than the threshold for capturing the left atrium. Therefore the electrode configuration being tested may not be selected for stimulating in the left atrium because the likelihood of cross-chamber capture would always be high.

Figure 7:
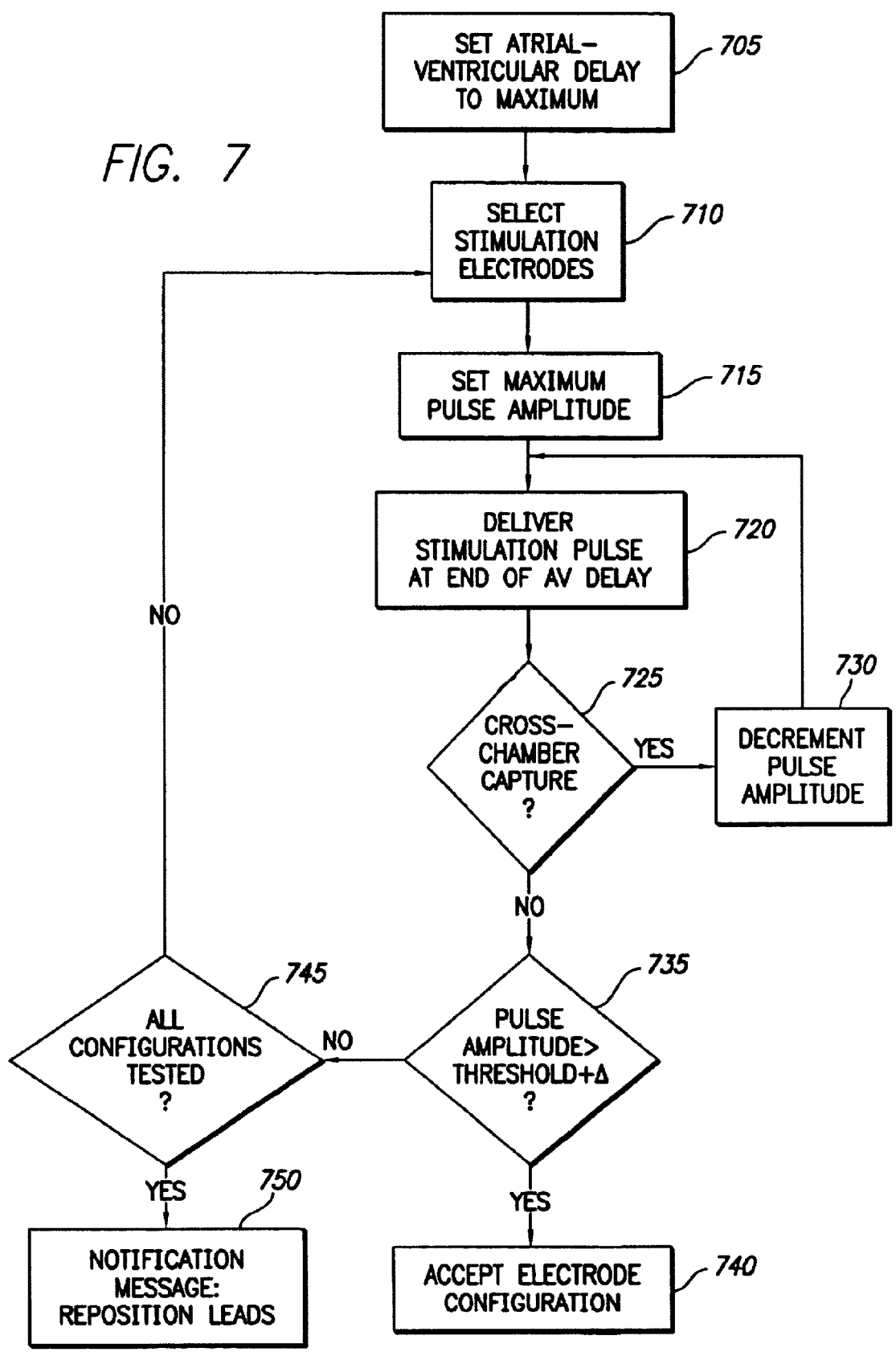
FIG. 7 is a flow chart describing an algorithm that may be used by the present invention during the operations of FIG. 3 for automatically determining left chamber cross-capture threshold.

In FIG. 7, an algorithm is shown which represents a subroutine performed at step 303 of method 300 for determining the cross-capture threshold when stimulating between selected electrode pairs for ventricular stimulation. At step 705, the atrial-ventricular (AV) delay is set to a maximum value (e.g., greater than about 250–350 milliseconds). This ensures that the ventricle will be stimulated outside of the physiological absolute refractory period of the atrium. To assess the risk of capturing the atrium during ventricular stimulation, the ventricular stimulation pulse must be delivered outside of atrial refractory.

At step 710, the electrode configuration that was found to result in the lowest ventricular capture threshold during subroutine 302 is selected first. The ventricular pulse energy is then set to a maximal setting at step 715 and a ventricular stimulation pulse is delivered at step 720 upon expiration of the next AV delay. At decision step 725, subroutine 303 determines if capture has occurred in only the left ventricle of if cross-chamber capture has occurred. This capture verification is done by setting simultaneous capture detection windows in both the left atrial channel and the left ventricular channel of device 10.

If atrial capture is detected, the ventricular stimulation pulse energy is decreased by one programmable setting, by decreasing either pulse amplitude or pulse width, at step 730. Subroutine 303 then returns to step 720 to deliver the next ventricular stimulation pulse at the new pulse energy output setting.

If atrial capture does not occur as determined at decision step 725, the current ventricular pulse output is compared to the capture threshold determined for the selected electrode configuration plus a predefined working margin at decision step 735. If the existing pulse energy is greater than the threshold plus a predefined working margin, then the electrode configuration is accepted at step 740.

If the existing pulse energy does not meet the minimum requirement as determined at decision step 735, the subroutine 303 determines if all available configurations have been tested at decision step 745. If not, the electrode configuration resulting in the second lowest capture threshold is selected at step 710 and steps 715 through 735 are repeated until an acceptable electrode configuration is found or until all configurations have been tested.

If all configurations have been tested as determined at decision step 745, then microprocessor 60 generates a message to be displayed on external device 102 notifying the medical practitioner that the leads should be repositioned because no suitable electrode configuration was found that reasonably avoided the risk of cross chamber stimulation, at step 750. If the method 300 is being performed automatically, the stimulation parameters may be adjusted in a way that avoids cross-chamber stimulation, such as setting a short AV delay so that the ventricle is always stimulated during the atrial refractory period, until the next physician visit.

The subroutine 303 will operate successfully in patients with complete conduction block between the atrial chamber and the ventricular chamber or as long as ventricular stimulation is not inhibited by detection of an intrinsic R-wave prior to the expiration of the extended AV interval. For patients with intact AV conduction in which continued R-wave sensing may preclude the execution of the subroutine 303, the ventricular stimulation pulse could be delivered via the selected electrodes at the time that the atrial stimulation pulse should be delivered with the atrial stimulation pulse being inhibited. This task may be achieved by triggering atrial pulse generator 70 to deliver the stimulation pulse to the selected electrode pair and inhibiting the ventricular pulse generator 72. The same steps can then be taken for determining if cross-chamber stimulation occurs, and, if so, whether the stimulation energy is greater than an acceptable minimum.

Likewise, testing for cross-chamber stimulation during atrial stimulation can be tested in the same manner as described in conjunction with FIG. 7, except that no adjustment to the AV delay as shown in step 705 is necessary, nor is there any requirement to wait for an AV delay as shown in step 720. Rather, the subroutine would begin by selecting a stimulation electrode configuration, determining atrial capture and ventricular capture thresholds for that configuration, and then repeating the process for each electrode configuration. The method then would select the electrode configuration resulting in the lowest atrial capture threshold as determined by subroutine 301, or the configuration with the largest ratio between the capture thresholds, or based on any other suitable criteria as described herein. If intrinsic atrial sensing is occurring, precluding the successful execution of the cross-chamber capture test, an adjustment of the base pacing rate to a temporary higher rate could be made in order to ensure atrial stimulation.

After cross-chamber capture testing has been performed and acceptable electrode configurations for atrial stimulation and for ventricular stimulation have been determined, method 300 proceeds to step 304 to select the optimal electrode configurations. At step 304, the electrode configurations found to be acceptable by subroutine 303 may be programmed in memory 94 as the new atrial stimulation configuration and the new ventricular stimulation configuration.

In alternative embodiments, the electrode configuration found to have the lowest atrial threshold during subroutine 301 and the highest ventricular threshold during subroutine 302 may be selected for the atrial stimulation configuration. Likewise, the electrode configuration found to have the lowest ventricular threshold during subroutine 302 and the highest atrial threshold during subroutine 301 may be selected for the ventricular stimulation configuration. It is recognized that different threshold criteria may be used for selecting the optimal stimulation electrode configurations without deviating from the scope of the present invention. Having reprogrammed the stimulation electrode configurations, method 300 is complete and is terminated at step 306.

Thus a method has been described that provides automatic selection of stimulation electrode configurations that minimize the risk of cross-chamber capture in dual chamber or multi-chamber stimulation applications. This method improves cardiac stimulation device performance by: increasing battery longevity by determining the minimum pulse energy required; reducing the risk of undesirable cross-chamber stimulation; and automating the electrode selection process. While the invention herein disclosed has been described according to specific embodiments and applications thereof, numerous modifications and variations could be made thereto by those skilled in the art without departing from the scope of the invention set forth in the claims.

What is claimed is:

1. In an implantable cardiac stimulation device, a method of setting a stimulation energy level, comprising:
   determining a primary capture threshold of a primary chamber using a predetermined stimulation electrode configuration;
   determining a cross-chamber capture threshold of a second chamber using the predetermined stimulation electrode configuration; and
   automatically setting the stimulation energy level based on the respective capture thresholds.

2. The method of claim 1, wherein determining a primary capture threshold comprises determining a primary capture threshold for an atrium.

3. The method of claim 1, wherein determining a primary capture threshold comprises determining a primary capture threshold for a ventricle.

4. The method of claim 1, wherein setting the stimulation energy level comprises setting an energy level between the respective capture thresholds.

5. The method of claim 1, further comprising determining primary and cross-chamber capture thresholds for a plurality of electrode configurations, and wherein setting comprises setting an optimal electrode configuration and stimulation energy level for the selected electrode configuration.

6. The method of claim 1, wherein setting the stimulation energy level comprises setting an energy level that exceeds the primary capture threshold by a predetermined amount.

7. The method of claim 1, wherein the predetermined electrode configuration comprises at least one electrode in a coronary sinus region.

8. The method of claim 7, wherein the predetermined electrode configuration comprises a unipolar configuration between an electrode in the coronary sinus region and a return electrode on a housing.

9. The method of claim 7, wherein the predetermined electrode configuration comprises a bipolar configuration between two electrodes in the coronary sinus region.

10. The method of claim 1, wherein the predetermined electrode configuration comprises at least one electrode in a right atrium.

11. The method of claim 5, wherein setting an optimal electrode configuration comprises setting an electrode configuration that provides an optimal ratio between the two capture thresholds.

12. The method of claim 5, wherein setting an optimal electrode configuration comprises setting an electrode configuration that provides 1) the lowest capture threshold for the primary chamber and 2) a differential between the respective capture thresholds that exceeds a predetermined amount.

13. A method of avoiding cross-chamber stimulation, for use with a cardiac stimulation device, comprising:
    defining primary chamber capture thresholds for a plurality of electrode configurations;
    determining cross-chamber capture thresholds for the plurality of electrode configurations; and
    automatically selecting an electrode configuration and stimulation energy level for the primary chamber stimulation based on the respective capture thresholds.

14. The method of claim 13, wherein the step of automatically selecting the electrode configuration comprises selecting an electrode configuration for capturing an atrium with minimal risk of causing capture of a ventricle.

15. The method of claim 13, wherein the step of automatically selecting the electrode configuration comprises selecting an electrode configuration for capturing a ventricle with minimal risk of causing capture of an atrium.

16. The method of claim 13, wherein the step of selecting the electrode configuration comprises selecting an electrode configuration that captures a left ventricle with minimal risk of causing capture of a left atrium.

17. The method of claim 13, wherein the step of selecting the electrode configuration comprises selecting an electrode configuration that captures a left atrium with minimal risk of causing capture of a left ventricle.

18. The method of claim 13, wherein the step of automatically selecting the electrode configuration comprises selecting an electrode configuration that results in a lowest primary capture threshold, and in a cross-capture threshold that exceeds the primary capture threshold by at least a predetermined amount.

19. The method of claim 15, further comprising delivering a ventricular stimulation pulse during a period when the atrium is not physiologically refractory.

20. A cardiac stimulation device capable of avoiding cross-chamber stimulation, comprising:
    a pulse generator that generates stimulation pulses;
    a lead system connected to the pulse generator, the lead system comprising:
        an atrial sense electrode that senses atrial cardiac signals;
        a ventricular sense electrode that senses ventricular cardiac signals;
        an atrial stimulation electrode that delivers atrial stimulation pulses to an atrium; and
        a ventricular stimulation electrode that delivers ventricular stimulation pulses to a ventricle; and
    a controller, connected to the lead system and pulse generator, that is responsive to signals from the respective sense electrodes to determine a primary chamber capture threshold for a plurality of electrode configurations, and that further determines cross-chamber capture thresholds for the plurality of electrode configurations, and wherein the controller automatically selects an electrode configuration for primary chamber stimulation based on the respective capture thresholds, such that a risk of cross-chamber stimulation is reduced.

21. The cardiac stimulation device of claim 20, wherein the electrode configuration captures an atrium with minimal risk of causing capture of a ventricle.

22. The cardiac stimulation device of claim 20, wherein the electrode configuration captures a ventricle with minimal risk of causing capture of an atrium.

23. The cardiac stimulation device of claim 20, wherein the electrode configuration results in a lowest primary chamber capture threshold, and in a cross-chamber capture threshold that exceeds the primary chamber capture threshold by at least a predetermined amount.

24. The cardiac stimulation device of claim 20, further comprising a memory that is operative to store a result of the respective capture threshold tests associated with each selected electrode configuration.

25. A cardiac stimulation device for selecting a stimulation energy level, comprising:
    means for determining a primary capture threshold of a primary chamber;
    means for determining a cross-chamber capture threshold of a second chamber; and
    means for selecting the stimulation energy level based on the respective capture thresholds.

26. The cardiac stimulation device of claim 25, wherein the means for selecting the stimulation energy selects a stimulation energy that is between the respective capture thresholds.

27. The cardiac stimulation device of claim 25, wherein the means for determining a primary capture threshold comprises means for determining an atrial capture threshold.

28. The cardiac stimulation device of claim 25, wherein the means for determining a primary capture threshold comprises means for determining a ventricular capture threshold.

29. A cardiac stimulation device comprising:
    a pulse generator that is operative to generate stimulation pulses;
    a lead system connected to the pulse generator, the lead system being operative to deliver stimulation pulses to at least one of an atrium and a ventricle, and to sense cardiac signals from at least one of the atrium and the ventricle; and
    a controller, connected to the lead system and pulse generator, that is operative to control the pulse generator to generate stimulation pulses that are applied to the heart by the lead system, the controller being responsive to sensed cardiac signals from the lead system to determine a primary chamber capture threshold and a cross-chamber capture threshold, and wherein the controller automatically selects a stimulation energy level based on the respective capture thresholds.

30. The cardiac stimulation device of claim 29, wherein the controller is operative to select a stimulation energy level between the respective capture thresholds.

31. The cardiac stimulation device of claim 29, wherein the controller is operative to determine a primary capture threshold for an atrium.

32. The cardiac stimulation device of claim 31, wherein the controller is operative to determine a primary capture threshold for a ventricle.

33. The cardiac stimulation device of claim 29, wherein the controller is operative to determine primary and cross-chamber capture thresholds for a plurality of electrode configurations, and wherein the controller is operative to select an optimal electrode configuration and stimulation energy level for the selected electrode configuration.

34. The cardiac stimulation device of claim 29, wherein the controller is operative to select an energy level that exceeds the primary capture threshold by a predetermined amount.

35. The cardiac stimulation device of claim 29, wherein the lead system comprises at least one electrode in a coronary sinus region.

36. The cardiac stimulation device of claim 29, wherein the lead system comprises at least one electrode in a right atrium.

37. The cardiac stimulation device of claim 33, wherein the controller is operative to select an electrode configuration that provides an optimal ratio between the two capture thresholds for use in applying stimulation energy to the heart.

38. The cardiac stimulation device of claim 33, wherein the controller is operative to select an electrode configuration for applying stimulation energy to the heart that provides 1) the lowest capture threshold for the primary chamber and 2) a differential between the respective capture thresholds that exceeds a predetermined amount.

* * * * *

UNITED STATES PATENT AND TRADEMARK OFFICE
CERTIFICATE OF CORRECTION

PATENT NO.    : 6,640,136 B1
DATED         : October 28, 2003
INVENTOR(S)   : John R. Helland and Gene A. Bornzin It is certified that error appears in the above-identified patent and that said Letters Patent is hereby corrected as shown below:

<u>Title page,</u>
Item [73], Assignee, should be:
-- PACESETTER, INC. --

Signed and Sealed this

Twenty-seventh Day of January, 2004

JON W. DUDAS
*Acting Director of the United States Patent and Trademark Office*